United States Patent [19]

Sugita et al.

[11] 4,324,630
[45] Apr. 13, 1982

[54] METHOD FOR FORMING A DENTAL CARIES PREVENTIVE COATING

[76] Inventors: Toshio Sugita, 17-12, Takamatsu-Cho 2-Chome, Tachikawa-Shi, Tokyo; Takanobu Morinushi, 19-1-205, Ogikubo 5-Chome, Suginami-Ku, Tokyo; Shigeharu Hanashima, 39-11, Mejirodai 1-Chome, Hachioji-Shi, Tokyo, all of Japan

[21] Appl. No.: 174,222

[22] Filed: Jul. 31, 1980

[30] Foreign Application Priority Data

Jul. 31, 1979 [JP] Japan .................................. 54/96741

[51] Int. Cl.³ ............................................. C23C 15/00
[52] U.S. Cl. .................................. 204/192 R; 427/2; 433/217

[58] Field of Search .................... 433/217; 204/192 C, 204/192 D, 192 S, 192 N, 192 R

[56] References Cited

U.S. PATENT DOCUMENTS

| | | | |
|---|---|---|---|
| 1,779,850 | 10/1930 | Maurer | 433/417 |
| 3,995,371 | 12/1976 | O'Keefe | 433/417 |
| 4,064,629 | 12/1977 | Stoner | 433/417 |

*Primary Examiner*—Sam Silverberg
*Attorney, Agent, or Firm*—Birch, Stewart, Kolasch and Birch

[57] ABSTRACT

In a discharge space are formed neutral or charged particles of metal, alloy, semiconductor or insulator. The particles thus formed are guided through a duct so that they reach a surface of a tooth and form a caries preventive coating covering the surface of the tooth.

1 Claim, 7 Drawing Figures

METHOD FOR FORMING A DENTAL CARIES PREVENTIVE COATING

BACKGROUND OF THE INVENTION

This invention relates to the improvement of oral hygiene, specifically to a method for forming a caries preventive coating for the purpose of reducing the degree to which teeth are affected by dental caries or decay.

It can be said that one of the most important clinical characteristics of dental caries is that they occur selectively on certain locations of teeth depending upon the type and portion of the teeth.

Among the different type of teeth, the molar teeth suffer most easily from caries, followed by upper and lower incisors. Among the permanent teeth, the first molar teeth are especially easily affected.

Among the parts of teeth pits and fissures of the molar teeth suffers most easily from caries, followed by their adjacent parts.

For the deciduous teeth, the situations are somewhat different from those described above for the permanent teeth and a more detailed and specific consideration of the teeth characteristics is needed. That is, among caries between adjacent teeth, those between superior middle incisors and between first and second deciduous molars are affected at a higher degree than the others. It is also another of the most prominent characteristics that, among the labial surfaces, the neck of the upper incisors are affected at a much higher degree than the other surfaces.

The characteristics described above can be advantageously utilized when searching for preventive measures. That is, it is possible to prevent caries more efficiently by taking preventive measures selectively for parts suffering more easily from caries by means of physical or chemical means.

Preventive or curative means against caries, which are brought into practice at present, are as follows:
 (A) Case of incisors
  (i) Fluorine coating
  (ii) Chemical plating
 (B) Case of permanent molars
  (i) Amalgam plugging
  (ii) Excavation and removal of affected part
  (iii) Resin plugging A technical disclosure about caries prevention is written in the following reference.
 E. I. Cueto and M. G. Buonocore "Sealing of Pits and Fissures with an adhesive Resin: It's use in caries prevention." J. of Amer. Dental Assoc. Vol. 75. P. 121-128, 1967

The traditional methods mentioned above have a common disadvantage that various substances cited above have an insufficient adhesion to the surface of teeth, thus they have little durable effect. According to the chemical plating process it is possible to obtain a relatively perferable adhesion due to its adhesion mechanism. However, the substance utilized for plating turns black as a result of the accompanying hardening reactions, by reacting with protein. Therefore, despite its fairly good durability, it has a disadvantage from patients' aesthetical point of view.

SUMMARY OF THE INVENTION

The object of this invention is, for the purpose of removing the disadvantages described above, to ameliorate qualitatively oral hygiene by forming a robust preventive coating for dental caries on the surface of teeth by simple means.

In order to achieve this object, it is necessary that satisfactory adherence to the surface of teeth and negligable penetration are obtained, that the coating procedure not depend on the shape of the affected part, and that the procedure can be easily put into practice.

Taking this object and these requirements into account, and after repeated searches and examinations for applicable caries preventive procedures and means for realizing them, the inventors of this invention have reached a conclusion that plating by cathode sputtering is easy to carry out and gives a robust coating having a satisfactory adhesion. In other words, the invention is based on a discovery of the effectiveness of ion sputtering, which is per se a known plating method, as a curative means against caries.

BRIEF DESCRIPTION OF THE DRAWINGS

The invention will be described more in detail, referring to the accompanying drawing, in which.

DETAILED DESCRIPTION OF THE INVENTION

Figure 1:
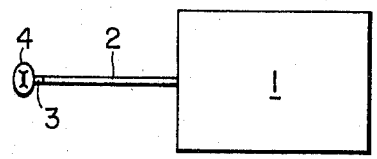
FIG. 1 is a schematic diagram of an apparatus, which can be used for bringing the method according to this invention into practice.
Figure 2A:
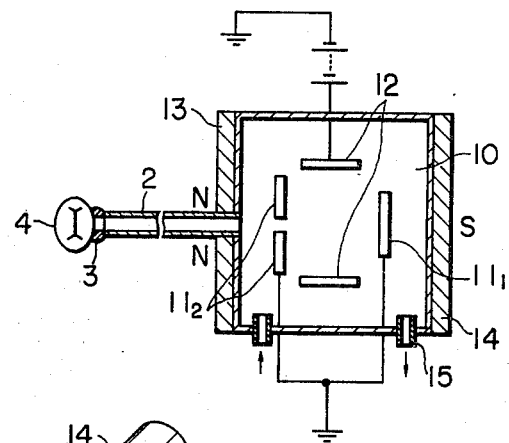
FIG. 2 (a) is an explicative cross-sectional view of an example of the apparatus shown in FIG. 1 and (b) is an exterior view of anodes and cathodes.
Figure 2B:
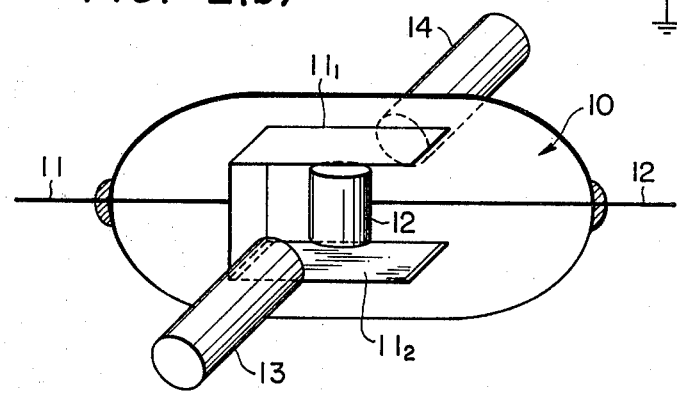
Figure 3A:
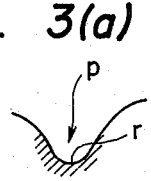
FIG. 3 contains views (a) and (b) for explaining the method according to the invention with corresponding views (c) and (d) for a traditional method.
Figure 3B:
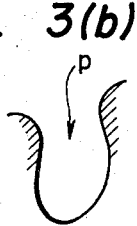
Figure 3C:
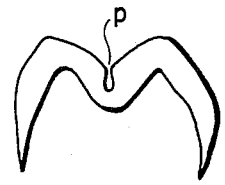
Figure 3D:
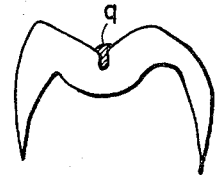

In FIG. 1, showing a fundamental concept of the invention, 1 is a space generating particles or atoms constituting coated film (hereinbelow called coater), 2 is a duct guiding coater to a surface to be coated, 3 is an airtight connecting element disposed at the extremity of the duct, and 4 is a tooth on which coater is to be adhered.

The generating space 1 consists of a body forming a discharge space 10, cathodes $11_1$, $11_2$ disposed in the body on the extension of the duct 2, anodes 12, 12 disposed between the two cathodes and substantially along the extended axis of the duct, and magnetic poles 13, 14 for giving drift motion to electrons produced by a potential difference between the electrodes. 15 denotes an evacuating pipe for medium gas.

In lieu of the cathodes described above it is also possible to utilize hollow cathodes.

Since the apparatus used for bringing the method according to this invention consists only of the constituent parts mentioned above, it can be made small in size and easily manageable as a dental curative apparatus.

In the above construction the cathodes 11 are made of gold, palladium, gold-palladium alloy, silicon, titanium carbide, titanium zirconate, etc. (hereinafter called simply gold etc.), and predetermined discharge is performed in the discharge space 10 filled with inert gas, such as argon, adjusted so that its pressure is about $10^{-4}$ Torr. Required conditions for the above sputtering of atoms of gold etc. are that the magnetic field strength be 1000 Gauss with the above mentioned inert gas, anode voltage be 2 kV, and the cathodes be grounded.

In the above construction, since atoms of gold etc. constituting the cathodes are bombarded by positive ions generated in the discharge space, the atoms evaporate and are guided through the duct 2 so as to reach the extremity of the duct where pressure is maintained at most at $10^{-2}$ Torr. Consequently, by applying the tightly fitting piece 3 (made for example of a vacuum gasket or rubber) disposed at the extremity of the duct 2 to a surface portion which is to be coated, a film made of gold etc. and having a shape limited by the tightly fitting piece 3 is formed on the surface portion.

Thus, according to this invention, it is possible to exclude completely all the causes of caries.

Since it is sufficient to form the film only on parts which suffer easily from caries and there are no other parts subject thereto, the method according to this invention is easily brought into practice and effective.

The method according to this invention can be compared for example with the curative measure called fissure sealant method (hereinbelow abbreviated to FS method) as follows. According to FS method, the surface of a pit and fissure p to be treated is roughened by using an oxidizing agent, then a pit thus formed should be filled with amalgam q, as shown in FIG. 3 (d). However, it is difficult to expect that the pit is filled perfectly with amalgam.

To the contrary, according to this invention, the following measures can be taken for any patient, adult or child. That is, a fissure p of a child is open as indicated in FIG. 3 (a) and the bottom r suffers easily from caries. A film according to this invention is formed on that surface. On the other hand, a fissure p of an adult as indicated in FIG. 3 (b) has a cavity with narrow entrance, and the walls of the cavity suffer easily from caries. Owing to characteristics of sputtering, this invention can be easily applied thereto so that a satisfactory caries preventive coating is formed on the surrounding wall of the cavity.

As explained above, since this invention consists of guiding particles such as atoms or molecules of a substance constituting a caries preventive coating directly to a part of a tooth which suffers especially easily from caries and depositing them thereon, and also owing to characteristics of sputtering, satisfactory adhesion of the coating with the surface of the tooth can be obtained. Moreover, since the procedures of the method are almost independent of the shape of the surface to which coater should be adhered, and the adherence of the film thus formed is perfect, the preventive treatments are simple and effective.

What is claimed is:

1. Method for forming a dental caries preventive coating by ion sputtering consisting of;
   forming neutral or charged particles of metal, alloy, semiconductor or insulator in a discharge space; and
   guiding said neutral or charged particles through a duct so that said particles reach selectively an limited portion of a tooth surface and form a coating covering said portion of the surface.

* * * * *